United States Patent
Miyawaki et al.

(10) Patent No.: US 9,453,897 B2
(45) Date of Patent: Sep. 27, 2016

(54) MAGNETIC RESONANCE IMAGING APPARATUS AND VIBRATIONAL ERROR MAGNETIC FIELD REDUCTION METHOD

(75) Inventors: Shouichi Miyawaki, Tokyo (JP); Hiroyuki Takeuchi, Tokyo (JP)

(73) Assignee: HITACHI MEDICAL CORPORATION, Tokyo (JP)

(*) Notice: Subject to any disclaimer, the term of this patent is extended or adjusted under 35 U.S.C. 154(b) by 779 days.

(21) Appl. No.: 13/817,680

(22) PCT Filed: Aug. 18, 2011

(86) PCT No.: PCT/JP2011/068650
§ 371 (c)(1),
(2), (4) Date: Feb. 19, 2013

(87) PCT Pub. No.: WO2012/026382
PCT Pub. Date: Mar. 1, 2012

(65) Prior Publication Data
US 2013/0147481 A1   Jun. 13, 2013

(30) Foreign Application Priority Data
Aug. 26, 2010   (JP) .................................. 2010-189068

(51) Int. Cl.
*G01R 33/58* (2006.01)
*G01R 33/389* (2006.01)
(Continued)

(52) U.S. Cl.
CPC ............... *G01R 33/58* (2013.01); *A61B 5/055* (2013.01); *G01R 33/56509* (2013.01); *G01R 33/56518* (2013.01)

(58) Field of Classification Search
CPC  A61B 5/055; G01R 33/3854; G01R 33/389; G01R 33/56509; G01R 33/56518; G01R 33/58

USPC .................................................. 324/300–322
See application file for complete search history.

(56) References Cited

U.S. PATENT DOCUMENTS

| 4,698,591 A * | 10/1987 | Glover ............. G01R 33/56518 324/307 |
| 5,289,127 A * | 2/1994 | Doddrell .......... G01R 33/56518 324/309 |

(Continued)

FOREIGN PATENT DOCUMENTS

| JP | 10-272120 | 10/1998 |
| JP | 2001-187040 | 7/2001 |

(Continued)

OTHER PUBLICATIONS

International Search Report in PCT/JP2011/068650.

*Primary Examiner* — Melissa Koval
*Assistant Examiner* — Rishi Patel
(74) *Attorney, Agent, or Firm* — Cooper & Dunham LLP

(57) ABSTRACT

Regardless of the measurement conditions, the degradation of the image quality due to a vibrational error magnetic field, which is generated by the vibration of the mechanical structure of an MRI apparatus, is reduced. In order to do so, error magnetic field image data indicating an error magnetic field distribution is acquired on the basis of an echo signal measured using a pulse sequence having a test gradient magnetic field, a parameter value of a damped vibration function showing a vibrational error magnetic field is calculated using the error magnetic field image data, and a correction magnetic field is calculated on the basis of the calculated parameter value of the damped vibration function showing the vibrational error magnetic field.

11 Claims, 11 Drawing Sheets

(51) Int. Cl.
   *G01R 33/565*   (2006.01)
   *A61B 5/055*   (2006.01)

(56) References Cited

U.S. PATENT DOCUMENTS

| | | |
|---|---|---|
| 5,770,943 A | 6/1998 | Zhou |
| 6,239,599 B1 * | 5/2001 | Zhou .................... G01R 33/58 |
| | | 324/307 |
| 6,380,738 B1 | 4/2002 | Zhou |
| 7,141,970 B2 | 11/2006 | Miyawaki et al. |
| 7,355,408 B2 * | 4/2008 | Takai ................. G01R 33/3854 |
| | | 324/318 |
| 2005/0218894 A1 * | 10/2005 | Miyawaki ........ G01R 33/56518 |
| | | 324/309 |
| 2012/0098535 A1 * | 4/2012 | Kaneta ............. G01R 33/56518 |
| | | 324/307 |

FOREIGN PATENT DOCUMENTS

| JP | 2004-261591 | 9/2004 |
|---|---|---|
| JP | 4106053 | 6/2008 |

* cited by examiner (a) EXAMPLE OF ABSOLUTE VALUE SPECTRUM: Y TO X COMPONENTS (b) EXAMPLE OF PHASE SPECTRUM: Y TO X COMPONENTS

MAGNETIC RESONANCE IMAGING APPARATUS AND VIBRATIONAL ERROR MAGNETIC FIELD REDUCTION METHOD

TECHNICAL FIELD

The present invention relates to a magnetic resonance imaging (hereinafter, referred to as MRI) apparatus that acquires a tomographic image of an arbitrary part of an object using nuclear magnetic resonance (hereinafter, referred to as NMR) phenomenon, and in particular, to a technique for correcting a vibrational error magnetic field due to the vibration of an MRI apparatus structure generated by the application of a gradient magnetic field.

BACKGROUND ART

The MRI apparatus is an apparatus that measures en NMR signal generated by the object, especially, the spin of nuclei which form human tissue, and images the shapes or functions of the head, abdomen, limbs, and the like in a two-dimensional manner or in a three-dimensional manner. In the imaging, different phase encoding is given to NMR signals by the gradient magnetic field and frequency encoding is also given to the NMR signals, and the NMR signals are measured as time-series data. The measured NMR signals are reconstructed as an image by a two-dimensional or three-dimensional Fourier transform.

When performing imaging on the basis of a predetermined pulse sequence in the above-described MRI apparatus, it is necessary to control the application time and strength of a gradient magnetic field accurately and freely, while selectively exciting a specific region. However, when a gradient magnetic field occurs, damping current is induced in a conductive structure around the gradient magnetic field coil. This is called an eddy current, and generates a magnetic field that changes spatially and temporally. As a result, the gradient magnetic field received by the object deviates from the ideal state, and this appears as various kinds of image quality degradation, such as image distortion, a reduction in the signal strength, and ghosting. Various methods for correcting the error magnetic field due to eddy current have been studied so far, and many have also been proposed as a patent.

On the other hand, when a gradient magnetic field is generated in the MRI apparatus, the Lorentz force due to the gradient magnetic field coil current spreads to the surrounding structure. The generation and dissipation of a gradient magnetic field in MRI imaging have a specific direction and occur frequently and periodically. Therefore, the force spreading to the surrounding structure also has directivity and periodicity. That is, it can be said that the MRI apparatus always "vibrates" in a certain direction and period while MRI imaging is being performed. In particular, this is a problem when the direction and period of vibration matches the natural frequency characteristics of the mechanical structure of the MRI apparatus. It is known that the vibrational error magnetic field caused by the resonance phenomenon of the mechanical structure has a strength having an influence on the image quality that cannot be neglected. MRI apparatuses in the related art have been designed firmly so that the resonance phenomenon does not occur or the mechanical structure is obtained in which the resonance phenomenon does not affect the image quality even if the resonance phenomenon occurs. In recent years, however, the need for a design allowing the occurrence of resonance has arisen from the perspective of product cost.

PTL 1 may be mentioned as one of the techniques for avoiding the vibrational error magnetic field due to the vibration of the mechanical structure. In the technique proposed in PTL 1, natural frequency information of a target MRI apparatus, which is obtained by performing measurement and analysis using a reference gradient magnetic field waveform, is stored in advance. In actual MRI imaging, the vibration of the mechanical structure caused by the execution of the pulse sequence is estimated on the basis of the measurement conditions set by the operator and the natural frequency information prepared in advance. Then, it is determined whether or not the estimated value of the vibration exceeds the allowable amount, and a change of the measurement conditions is prompted if the estimated value of the vibration exceeds the allowable amount.

CITATION LIST

Patent Literature

[PTL 1] JP-A-2005-270326
[PTL 2] Japanese Patent No. 4106053
[PTL 3] U.S. Pat. No. 4698591
[PTL 4] PCT International Publication No. WO2004/004563
[PTL 5] PCT International Publication No. WO2010/143586

SUMMARY OF INVENTION

Technical Problem

However, given that the combination of the gradient magnetic field waveform determined by the measurement conditions is infinite, it is considered that it is difficult to accurately estimate all vibrations of the mechanical structure, which are actually caused, on the basis of the natural frequency information prepared in advance. In addition, waiting time required for internal processing (calculation) to estimates caused vibration occurs before the operator starts measurement, and asking for a change of imaging conditions if the measurement conditions are not suitable, is not desirable for clinical use. In addition, given that the FSE (Fast Spin Echo) sequence used in most of the clinical measurement is significantly influenced by the vibrational error magnetic field, it is thought that many issues to be solved are left for practical use of this technique.

Therefore, the present invention has been made in view of such a problem, and it is an object of the present invention to provide an MRI apparatus and a vibrational error magnetic field reduction method capable of reducing the degradation of the image quality due to the vibrational error magnetic field, which is generated by the vibration of the mechanical structure of the MRI apparatus, regardless of the measurement conditions.

Solution to Problem

The present invention has been made in order to achieve the above-described object, and the present invention acquires error magnetic field image data indicating an error magnetic field distribution on the basis of an echo signal measured using a pulse sequence having a test gradient magnetic field, calculates a parameter value of a damped vibration function showing a vibrational error magnetic field using the error magnetic field image data, and calculates a correction magnetic field on the basis of the calculated parameter value of the damped vibration function showing the vibrational error magnetic field. This parameter value is a characteristic value indicating the vibration characteristic of each MRI apparatus.

Specifically, an MRI apparatus of the present invention includes: a static magnetic field generation unit that generates a static magnetic field in imaging space; a gradient magnetic field generation unit that generates a gradient magnetic field so as to be superimposed on the static magnetic field; a correction magnetic field generation unit that generates a correction magnetic field for correcting an error magnetic field generated in the imaging space due to application of the gradient magnetic field; a structural unit that supports the static magnetic field generation unit, the gradient magnetic field generation unit, and the correction magnetic field generation unit mounted inside; a measurement control unit that measures an echo signal from an object disposed in the imaging space on the basis of a predetermined pulse sequence; and a correction magnetic field calculation unit that calculates a correction magnetic field for correcting an error magnetic field generated in the imaging space due to application of the gradient magnetic field. The correction magnetic field calculation unit calculates an error magnetic field including a vibrational error magnetic field based on vibration of the structural unit due to application of the gradient magnetic field, and calculates the correction magnetic field for correcting the calculated error magnetic field.

In addition, a vibrational error magnetic field reduction method of the present invention includes: a measurement step of measuring an echo signal using a pulse sequence having a test gradient magnetic field; a step of acquiring error magnetic field image data, which indicates an error magnetic field distribution at each sampling time, using an echo signal; a parameter value calculation step of calculating a parameter value of a damped vibration function showing a vibrational error magnetic field using error magnetic field image data at each sampling time; and a correction magnetic field calculation step of calculating a correction magnetic field on the basis of the calculated parameter value of the damped vibration function showing the vibrational error magnetic field.

Advantageous Effects of Invention

According to the MRI apparatus and the vibrational error magnetic field reduction method of the present invention, it is possible to reduce the degradation of the image quality due to the vibrational error magnetic field, which is generated by the vibration of the mechanical structure of the MRI apparatus, regardless of the measurement conditions.

In addition, by this effect, it is possible to improve the degree of freedom in the mechanical structure design of the MRI apparatus and to allow a certain amount of vibration. Accordingly, there is also a secondary effect that the material cost of the MRI apparatus can be reduced.

BRIEF DESCRIPTION OF DRAWINGS

FIG. 11(a) is an image obtained without performing the vibrational error magnetic field reduction processing of the present invention and FIG. 11(b) is an image obtained by performing the vibrational error magnetic field reduction processing of the present invention.

DESCRIPTION OF EMBODIMENTS

Figure 1:
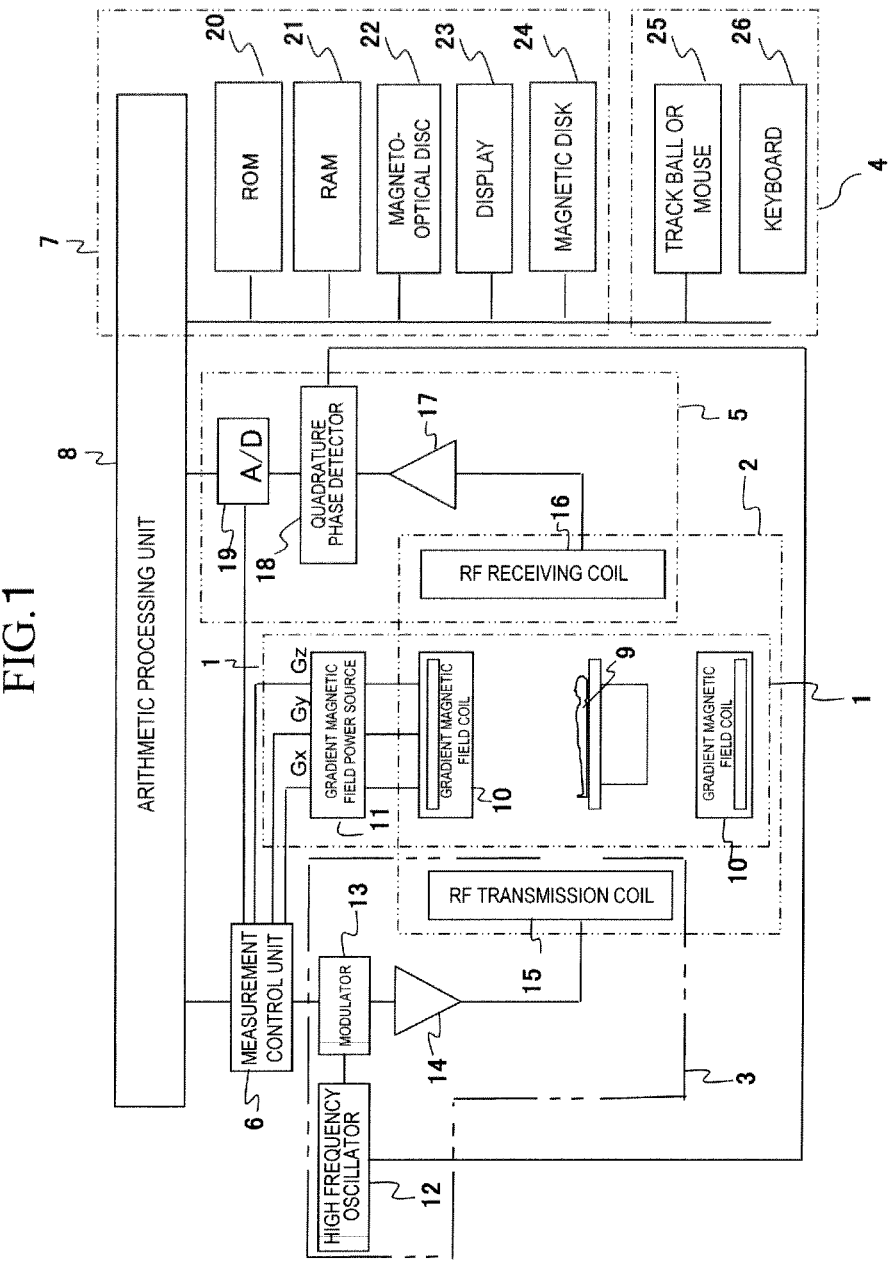
FIG. 1 is a block diagram showing the overall configuration of an example of an MRI apparatus in the present invention.

Hereinafter, preferred embodiments of an MRI apparatus of the present invention will be described in detail according to the accompanying drawings. In addition, in all drawings for explaining the embodiments of the invention, the same reference numerals are given to those with the same functions, and repeated explanation thereof will be omitted.

First, the outline of an example of an MRI apparatus according to the present invention will be described on the basis of FIG. 1. FIG. 1 is a block diagram showing the overall configuration of an embodiment of the MRI apparatus according to the present invention. This MRI apparatus acquires a tomographic image of en object using an NMR phenomenon. As shown in FIG. 1, the MRI apparatus is configured to include a static magnetic field generation system 2, a gradient magnetic field generation system 1, a signal transmission system 3, a signal receiving system 5, a signal processing system 7, a measurement control unit 6, an arithmetic processing unit 8, and a correction magnetic field calculation unit 200.

The static magnetic field generation system 2 generates a uniform static magnetic field around an object 9 in the body axis direction or in a direction perpendicular to the body axis, and permanent magnet type, normal conduction type, or superconducting type magnetic field generation means not shown) is disposed in a certain spread space around the object 9.

The gradient magnetic field generation system 1 includes gradient magnetic field coils 10 wound in three axial directions of X, Y, and Z and a gradient magnetic field power source 11 which drives each coil 10, and applies gradient magnetic fields Gs, Gp, and Gf in the three axial directions of X, Y, and Z, to the object 9 by driving the gradient magnetic field power source 11 of each coil according to a command from the measurement control unit 6 to be described later.

At the time of imaging of the two-dimensional slice surface, a slice gradient magnetic field pulse (Gs) is applied in a direction perpendicular to the slice surface (imaging cross-section) so that a slice surface of the object 9 is set, and a phase encoding gradient magnetic field pulse (Gp) and a frequency encoding gradient (readout) magnetic field pulse (Gf) are applied in the two remaining directions, which are perpendicular to the slice surface and are also perpendicular to each other, so that the positional information in each direction is encoded in an NMR signal (echo signal).

In addition, from the spatial and temporal information of an eddy current due to the application of a gradient magnetic field, an error magnetic field due to a residual magnetic field, or an error magnetic field due to vibration, each of the above error magnetic fields is reduced by applying a correction current to a shim coil or a localized coil, which forms a part of the static agnetic field generation system 2, or to the gradient magnetic field generation system 1.

The signal transmission system 3 emits a high frequency magnetic field (hereinafter, referred to as RF) pulse in order to cause an NMR phenomenon in nuclei of atoms which form the body tissue of the object 9, and is configured to include a high frequency oscillator 12, a modulator 13, a high frequency amplifier 14, and a transmission-side RF transmission coil 15. Specifically, the high frequency oscillator 12 is driven according to a command from the measurement control unit 6, which will be described, to generate a high frequency pulse, and the high frequency pulse is amplitude-modulated by the modulator 13 and is amplified by the high frequency amplifier 14. Then, the amplified pulse is supplied to the RF transmission coil 15 disposed near the object 9. As a result, the RF pulse is emitted to the object 9.

The signal receiving system 5 detects an echo signal (NMR signal) emitted by the NMR phenomenon of nuclei, which forms the body tissue of the object 9, and includes a receiving-side RF receiving coil 16, an amplifier 17, a quadrature phase detector 18, and an A/D converter 19. A response electromagnetic wave (NMR signal) of the object 9 induced by the electromagnetic wave emitted from the RF transmission coil 15 is detected by the RF receiving coil 16 disposed near the object 9, is input to the A/D converter 19 through the amplifier 17 and the quadrature phase detector 18, and is converted into a digital amount. Then, the digital mount becomes two series of collection data sampled by the quadrature phase detector 18 at the timing based on the command from the measurement control unit 6, and this signal is transmitted to the signal processing system 7.

The signal processing system 7 performs image display and image reconstruction operation using the echo signal detected by the signal receiving system 5, and includes: the arithmetic processing unit 8 that performs processing, such as a Fourier transform, correction coefficient calculation, and image reconstruction, on an echo signal and control of the measurement control unit 6; a ROM (read only memory) 20 that stores a program for performing temporal image analysis processing and measurement, invariant parameters used in its execution, and the like; a RAM (random access memory) 21 that temporarily stores measurement parameters obtained by pre-measurement, an echo signal detected by the signal receiving system 5, and an image used for the setting of a region of interest and also stores parameters for setting the region of interest and the like; a magneto-optical disc 22 and a magnetic disk 24 serving as a data storage unit that stores the image data reconstructed by the arithmetic processing unit 8; and a display 23 serving as a display unit that visualizes the image data read from the magneto-optical disc 22 or the magnetic disk 24 and displays it as a tomographic image.

The measurement control unit 6 is control means for controlling the measurement of an echo signal from the object 9 by repeatedly applying an RF pulse and a gradient magnetic field pulse on the basis of a predetermined pulse sequence, and operates under the control of the arithmetic processing unit 8 and transmits various commands, which are required for the data collection of the tomographic image of the object 9, to the signal transmission system 3, the shim coil or the localized coil which forms a part of the static magnetic field generation system 2, the gradient magnetic field generation system 1, and the signal receiving system 5.

In addition, an operating unit 4 is for inputting the control information of the processing performed by the signal processing system 7, and includes a track ball or a mouse 25 and a keyboard 26. This operating unit 4 is disposed near the display 23, so that the operator controls various kinds of processing of the MRI apparatus interactively through the operating unit 4 while observing the display 23.

Currently, nuclides imaged by an MRI apparatus, which are widely used clinically, are a hydrogen nucleus (proton) which is a main component material of the object. The shapes or functions of the head, abdomen, limbs, and the like of the human body are imaged in a two-dimensional or three-dimensional manner by performing imaging of the information regarding the spatial distribution of the proton density or the spatial distribution of the relaxation time of the excited state.

As the events that led to the creation of the present invention, the inventor has discovered that a component of an error magnetic field due to the vibration of the mechanical structure (hereinafter, referred to as a vibrational error magnetic field) of an MRI apparatus is superimposed on a measurement result of an error magnetic field due to eddy current (hereinafter, referred to as an eddy current error magnetic field). In a conventional (known) method of measuring the eddy current error magnetic field, the response of the MRI apparatus with respect to the test gradient magnetic field applied in advance is measured. For this reason, it is natural that the measurement result includes not only the eddy current error magnetic field but also the vibrational error magnetic field due to the test gradient magnetic field.

Therefore, the inventor has thought of the MRI apparatus and the vibrational error magnetic field reduction method of the present invention for correcting both the eddy current error magnetic field generated by the application of the gradient magnetic field and the vibrational error magnetic field due to the vibration of the structure of the MRI apparatus. One embodiment thereof will be described in detail below.

Figure 2:
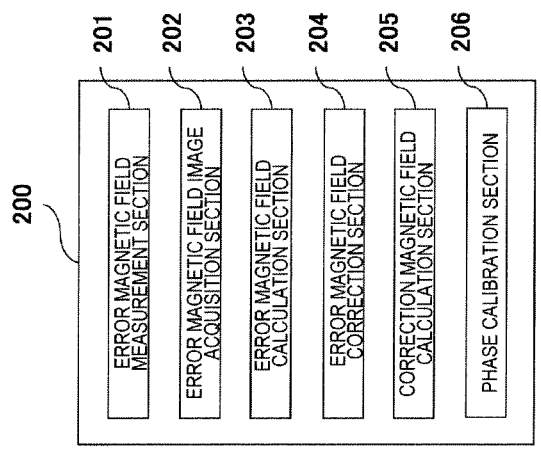
FIG. 2 is a functional block diagram of a correction magnetic field calculation unit 200.
Figure 3:
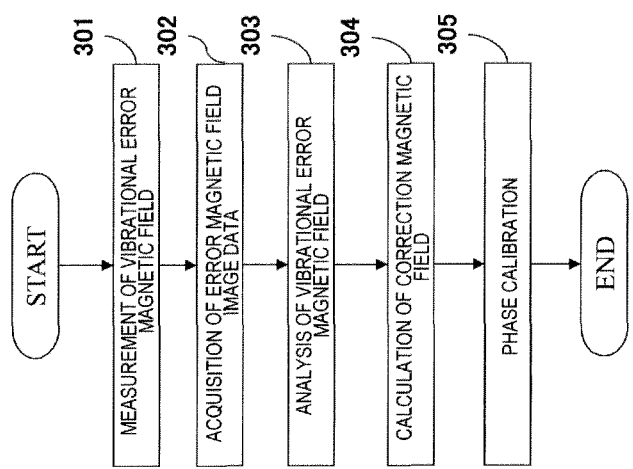
FIG. 3 is a flow chart showing the process flow when functional sections of the correction magnetic field calculation unit 200 function together to correct a vibrational error magnetic field.

First, each function of the correction magnetic field calculation unit 200 that calculates and outputs a correction magnetic field for correcting a vibrational error magnetic field according to the present embodiment will be described on the basis of a functional block diagram of the correction magnetic field calculation unit 200 shown in FIG. 2. The correction magnetic field calculation unit 200 according to the present embodiment includes an error magnetic field measurement section 201, an error magnetic field image acquisition section 202, an error magnetic field calculation section 203, an error magnetic field correction section 204, a correction magnetic field calculation section 205, and a phase calibration section 206. These sections are mounted in the measurement control unit 6 or the arithmetic processing unit 8. In addition, these sections cooperate with each other to perform processing for correcting the vibrational error magnetic field shown in the flow chart of FIG. 3. Hereinafter, the outline of vibrational error magnetic field correction processing of the present embodiment will be described on the basis of the flow chart of FIG. 3.

In step 301, a vibrational error magnetic field is measured. The error magnetic field measurement section 201 generates a predetermined measurement sequence and causes the measurement control unit 6 to execute it to measure an echo signal on which a vibrational error magnetic field is superimposed, thereby acquiring an echo signal on which a vibrational error magnetic field is superimposed. This will be described in detail later.

In step 302, time-series error magnetic field image data is acquired using the echo signal acquired in step 301. The error magnetic field image acquisition section 202 acquires a complex image every sampling time of the echo signal by performing a Fourier transform of the echo signal acquired in step 301 in a spatial axis direction, and calculates a phase image from each complex image to acquire time-series phase image data. In addition, the error magnetic field image acquisition section 202 acquires time-series error magnetic field image data from the time-series phase image data. This will be described in detail later.

In step 303, vibrational error magnetic field analysis is performed using the time-series phase image data acquired in step 302. Details of the vibrational error magnetic field analysis will be described later.

In step 304, using the result of the vibrational error magnetic field analysis in step 303, a correction magnetic field for correcting the vibrational error magnetic field according to the input gradient magnetic field waveform is calculated. Details of the calculation of the correction magnetic field will be described later.

In step 305, the phase calibration of the correction magnetic field calculated in step 304 is performed. Details of the phase calibration will be described later.

Until now, the process flow of the present embodiment has been described. Hereinafter, details of each step will be described.

(1. Vibrational Error Magnetic Field Measurement)

Next, details of the vibrational error magnetic field measurement in step 301 will be described.

The vibrational error magnetic field due to the vibration of the MRI apparatus structure, which is induced by the application of a gradient magnetic field, has frequency distribution. Therefore, in order to measure the target frequency component correctly, it is necessary to measure an echo signal, on which the vibrational error magnetic field is superimposed, using a pulse sequence having optimal time resolution and measurement window (sampling time). Therefore, as known measurement methods that meet this demand, a method using a measurement sequence suitable for the measurement of a low frequency component of the vibrational error magnetic field and a method using a measurement sequence suitable for the measurement of a high frequency component of the vibrational error magnetic field will be described below.

Moreover, in any of the following methods, in the measurement of a vibrational error magnetic field, an echo signal on which the information of only the vibrational error magnetic field is superimposed may be measured in a state, in which the eddy current error magnetic field has been corrected in advance, to acquire the information of only the vibrational error magnetic field, or an echo signal on which the information of both the eddy current error magnetic field and the vibrational error magnetic field is superimposed may be measured without correcting the eddy current error magnetic field to acquire these information items simultaneously. When both the information items are simultaneously acquired, the eddy current error magnetic field and the vibrational error magnetic field are corrected without distinction.

(1.1 Measurement of a Low Frequency Component)

In the measurement of a component having a low frequency of about 10 to 20 [Hz] or less, it is necessary to measure an error magnetic field variation over a sufficiently long period of time. The measurement method disclosed in PTL 2 is suitable for this. In this method, there is no restriction in the measurement window (measurement time). Accordingly, even if the frequency of the error magnetic field variation is close to 0 as possible or even if the damping time is very long, it is possible to measure the error magnetic field variation significantly.

In order to eliminate the influence of the error magnetic field due to the gradient magnetic field for measuring an echo signal and the influence of non-uniformity of the static magnetic field, a difference between echo signals and images after a Fourier transform of the echo signals may be acquired between two measurements, in which the polarities of the test gradient magnetic field are reversed, or between two measurements of a measurement with a test gradient magnetic field and a measurement with no test gradient magnetic field.

In the method disclosed in PTL 2, however, there is an upper limit to the frequency that can be measured since the time resolution is determined by the repetition time TR. Therefore, it is preferable to use a method, which will be described later, for a high frequency component.

The error magnetic field measurement section 201 generates the pulse sequence by calculating data which specifically defines the application timing and application strength, sampling timing, or the like of the gradient magnetic field pulse including the test gradient magnetic field and the RF pulse, which form the pulse sequence disclosed in PTL 2. Then, the error magnetic field measurement section 201 notifies the measurement control unit 6 of the calculated data and causes the measurement control unit 6 to execute the pulse sequence to measure an echo signal on which the vibrational error magnetic field is reflected. In addition, when performing two measurements in which the polarities of the test gradient magnetic field are reversed or two measurements of a measurement with a test gradient magnetic field and a measurement with no test gradient magnetic field, the error magnetic field measurement section 201 generates each pulse sequence and causes the measurement control unit 6 to execute the pulse sequence, thereby measuring echo signals with different test gradient magnetic fields and acquiring a difference between echo signals or images after a Fourier transform of the echo signals.

(1.2 Measurement of a High Frequency Component)

As one of methods of measuring a high frequency component, a technique disclosed in PTL 3 may be mentioned in which a test gradient magnetic field is applied in advance and high frequency excitation is performed immediately after the application or after the passage of predetermined time to measures an echo signal.

Figure 4:
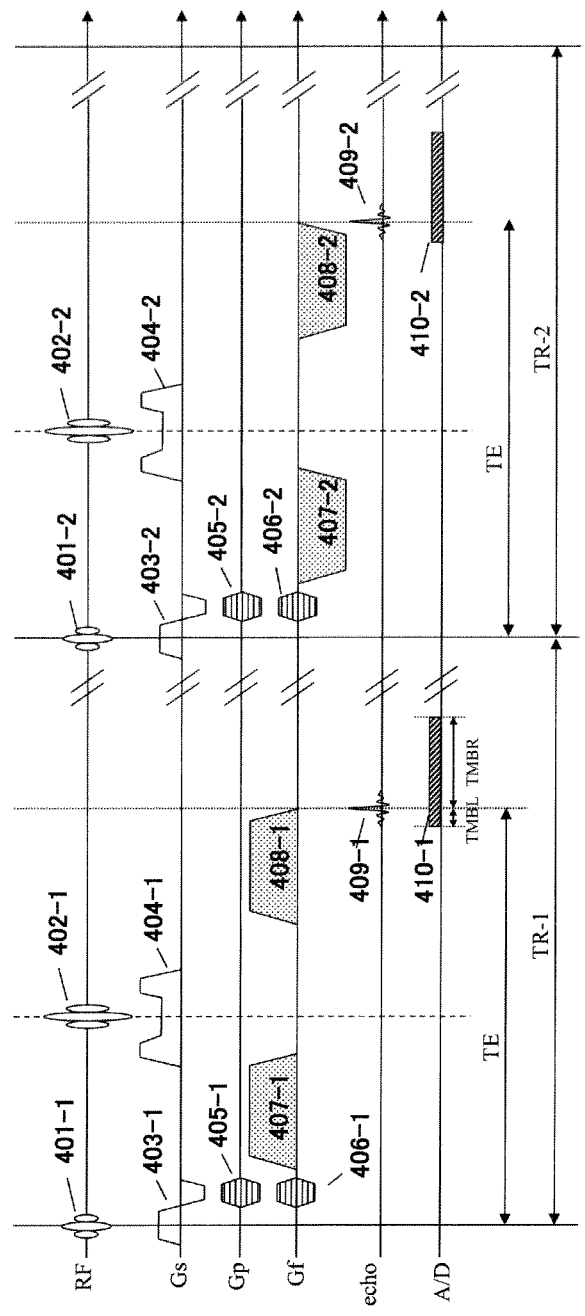
FIG. 4 is a view showing a pulse sequence suitable for the measurement of a high frequency component of the vibrational error magnetic field.

As another method, a measurement sequence shown in FIG. 4 may be used. This measurement sequence is based on the Spin Echo sequence. RF, Gs, Gp, Gf, Echo, and A/D indicate axes of an RF pulse, a slice gradient magnetic field, a phase encoding gradient magnetic field, a frequency encoding gradient magnetic field, an echo signal, and a sampling period, respectively. FIG. 4 shows a sequence chart of 2 repeats, and the first half is expressed with a subscript "−1" and the second half is expressed with a subscript "−2". In addition, within 1 repetition time (TR), an RF pulse 401 for 90° excitation and a slice selection gradient magnetic field pulse 403 are applied approximately simultaneously to excite the spin of a desired imaging region, positional information is encoded in the phase of the spin excited by applying an encoding gradient magnetic field pulse 405 in a phase encoding direction and an encoding gradient magnetic field pulse 406 in a frequency encoding direction, an echo signal is formed by applying a 180° re-convergence RE pulse 402 and a slice selection gradient magnetic field pulse 404 approximately simultaneously so that the phase of the spin is re-converged, and the echo signal is measured in a sampling period 410.

In such a Spin Echo sequence, test gradient magnetic fields 407 and 408, of which the amounts of application are the same, are applied before and after the re-convergence RF pulse 402 in a physical axis direction (in the example shown in FIG. 4, a frequency encoding direction) in which the error magnetic field is measured. In order to set the strength of the test gradient magnetic field 408 to zero immediately before the time TE, an echo signal on which an error magnetic field induced by this test gradient magnetic field (caused by eddy current or mechanical vibration) is superimposed is sampled immediately after the time or after the passage of predetermined time.

In order to eliminate the influence of the error magnetic field due to the gradient magnetic fields 403, 404, 405, 406, and 407 for two-dimensional imaging and the influence of non-uniformity of the static magnetic field in the error magnetic field measurement sequence described above, the measurement of each echo signal is performed by changing (that is, reversing) the polarities of the test gradient magnetic fields 407 and 408 or according to the presence of a test gradient magnetic field. For this reason, in another repetition time (TR), the polarities of the test gradient magnetic fields 407 and 408 are reversed, and others excluding the test gradient magnetic fields 407 and 408 are assumed to keep previous polarities. It is assumed that measurement when the test gradient magnetic fields 407 and 408 have a positive polarity is Scan (+) and measurement when the test gradient magnetic fields 407 and 408 have a negative polarity is Scan (−). Alternatively, measurement with a test gradient magnetic field may be set as Scan (+) and measurement with no test gradient magnetic field may be set as Scan (−), or vice versa.

Figure 5:
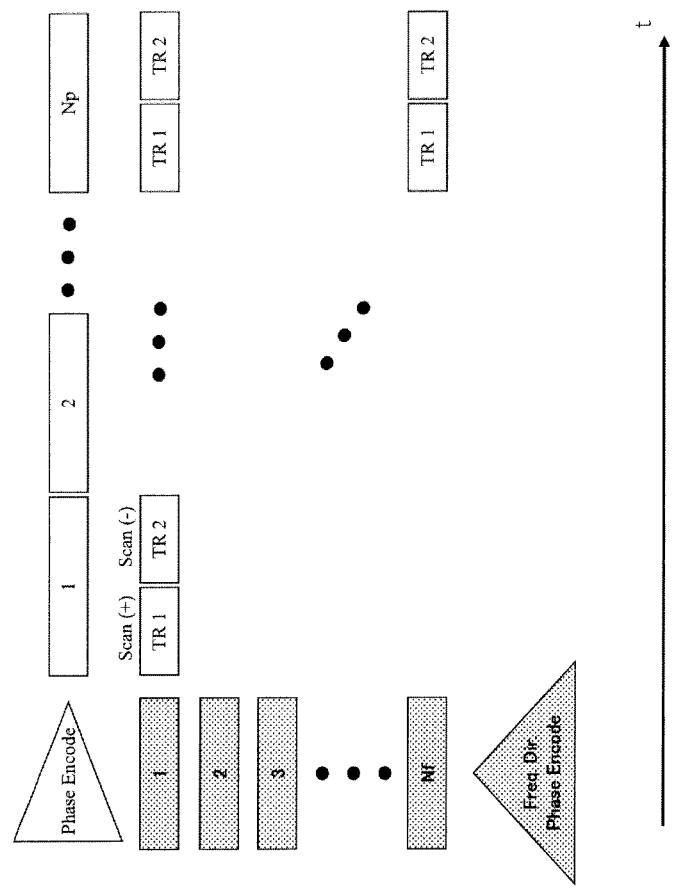
FIG. 5 is a view showing an example of the sequence for performing Scan (+) and Scan (−) for each phase encoding value in order to measure an echo signal in the pulse sequence of FIG. 4.

For echo signal measurement, as shown in FIG. 5, Scan (+) and Scan (−) are sequentially performed for each phase encoding value, and this is repeated a number of times required for two-axis phase encoding of the excitation cross-section (Np*Nf times). In addition, the polarity reversal of test gradient magnetic fields may not be alternately performed. After ending the measurement of one test gradient magnetic field, the polarity of the test gradient magnetic field may be reversed to repeat the measurement.

In this error magnetic field measurement sequence shown in FIG. 4, it is not necessary to perform excitation using an RF pulse after the application of the test gradient magnetic field, unlike the error magnetic field measurement sequence disclosed in PTL 3. Therefore, there is an advantage in that the error magnetic field can be measured during the application of the gradient magnetic field or immediately after the strength of the gradient magnetic field becomes zero.

In the two methods described above, the frequency resolution with respect to the vibrational error magnetic field is determined by the bandwidth (BW) of the sampling of the echo signal, and the measurement capability of the low frequency side is determined by echo signal acquisition time (window time).

The error magnetic field measurement section 201 generates the above-described error magnetic field measurement sequence, which is disclosed in PTL 3 or PTL 4, and causes the measurement control unit 6 to execute the error magnetic field measurement sequence to measure an echo signal on which the error magnetic field is superimposed.

(Acquisition of a Time-Series Phase Image)

Next, details of the acquisition of time-series phase image data in step 302 will be described on the basis of the flowchart shown in FIG. 6. In addition, this time-series phase image data acquisition processing is performed in both of the two methods (low frequency component measurement and high frequency component measurement) described in the above vibrational error magnetic field measurement.

Figure 6:
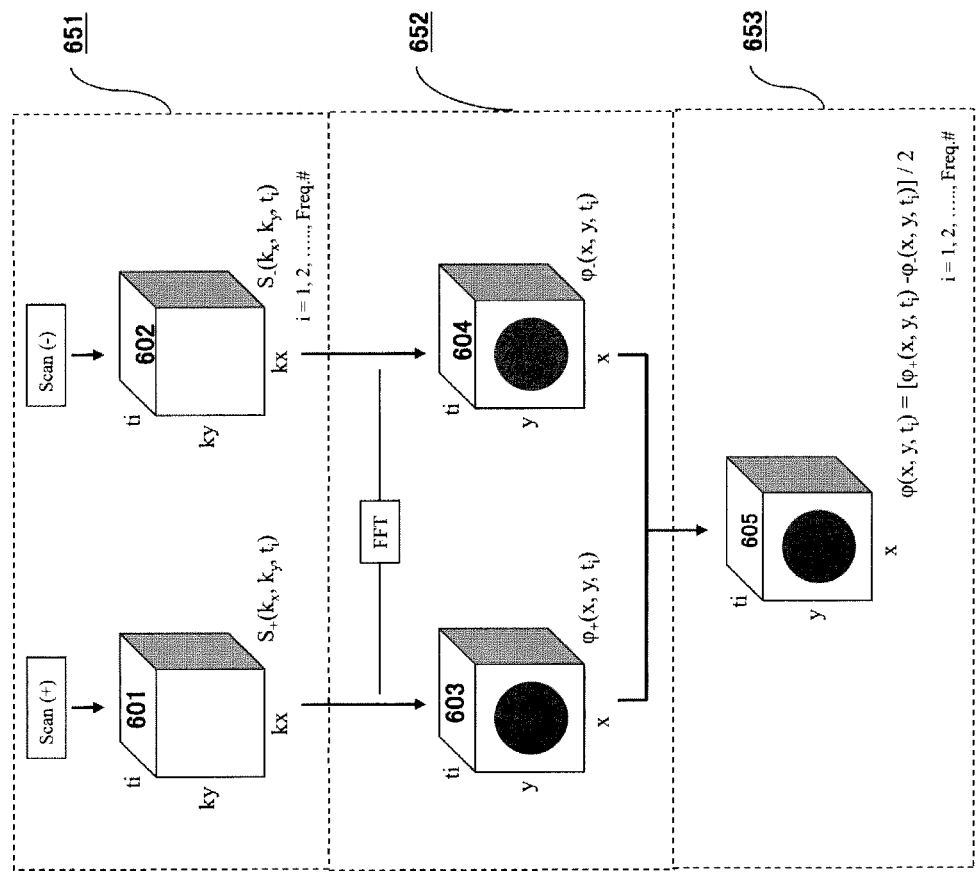
FIG. 6 is a flow chart showing the process flow for acquiring time-series phase image data.

In step 651, the error magnetic field image acquisition section 202 divides the echo signal measured in step 301 into three-dimensional data sets S+(kx, ky, ti) and S−(kx, ky, ti) of Scan (+) and Scan (−) shown in 601 and 602 of FIG. 6. Here, kx and ky are spatial frequencies in the frequency encoding direction and the phase encoding direction, respectively, and ti indicates a discrete time point (i=1, 2, . . . , n) of the sampled echo signal. A time interval (time resolution) in the ti direction is uniquely determined by the sampling frequency, and the number of data items is uniquely determined by the resolution Freq.# in the frequency direction.

In step 652, the error magnetic field image acquisition section 202 performs a two-dimensional Fourier transform of the two data sets S+ and S− separately at each time ti with kx and ky as variables, thereby obtaining two-dimensional complex images I+(x, y, ti) and I−(x, y, ti) at each time. Using these two-dimensional complex images, phase images $\phi$+(x, y, ti) and $\phi$−(x, y, Si) at each time ti are created (603, 604).

In step 653, the error magnetic field image acquisition section 202 takes a difference between the two phase image data items $\phi$+(x, y, ti) and $\phi$−(x, y, ti) in order to create a data set $\phi$(x, y, ti) (605) of a phase image from which the influence of the error magnetic field due to the gradient magnetic fields 403, 404, 405, 406, and 407 for performing imaging and the influence of non-uniformity of the static magnetic field are eliminated.

The phase image data when two measurements (two-pole measurement) are performed by inverting the test gradient magnetic field is $\phi$(x, y, ti)=[$\phi$+(x, y, ti)−$\phi$−(x, y, ti)]/2, and the phase image data in the case of single pole measurement is $\phi$(x, y, ti)=$\phi$+(x, y, ti)−$\phi$−(x, y, ti). FIG. 6 shows a case of two-pole measurement. A phase based on the vibrational error magnetic field with attenuation due to the vibration of the MRI apparatus structure induced by the application of the gradient magnetic field is reflected in the phase image data calculated as described above.

Finally, vibrational error magnetic field image data Be(x, y, ti) can be calculated as follows on the basis of the fact that the phase of the phase image and the magnetic field strength are proportional to each other.

$$Be(x,y,ti)=\phi(x,y,ti)/(\gamma ti)$$

Here, $\gamma$ is a gyromagnetic ratio. If this calculation is performed every time ti, it is possible to acquire the vibrational error magnetic field image data indicating the error magnetic field distribution at each sampling time.

Although the processing of acquiring the vibrational error magnetic field data every sampling time has been described up to now, it is possible to acquire the error magnetic field as two-dimensional or three-dimensional spatial information using the two methods (low frequency component measurement and high frequency component measurement) shown above. However, when such specific spatial information is not required, it is sufficient to just measure the error magnetic field at the specific space coordinates shown in PTL 4 or PTL 5.

(Analysis of the Vibrational Error Magnetic Field)

Next, details of the vibrational error magnetic field analysis in step 303 will be described.

Figure 7:
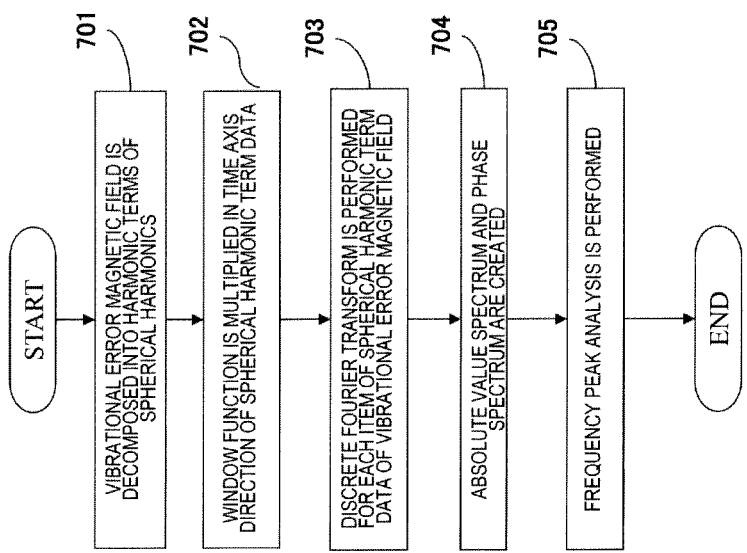
FIG. 7 is a flow chart showing the process flow of the vibrational error magnetic field analysis.

The error magnetic field calculation section 203 performs an analysis for calculating the frequency distribution of each space component of the vibrational error magnetic field data, which is acquired by the vibrational error magnetic field measurement described above, on the basis of the flow chart shown in FIG. 7. Hereinafter, processing in each step will be described in detail.

In step 701, the error magnetic field calculation section 203 decomposes the vibrational error magnetic field Be(x, y, ti) at each time ti acquired in step 653 into terms of spherical harmonics (hereinafter, referred to as spherical harmonic terms) in each direction (X, Y, Z) in which the test gradient magnetic field is applied. That is, the vibrational error magnetic field Be(x, y, ti) at all time ti is decomposed into spherical harmonic terms as follows.

$$Be(x,y,ti) = \zeta_{0,0}(ti) + \zeta_{1,-1}(ti)y + \zeta_{1,0}(ti)z + \zeta_{1,1}(ti)x + \zeta_{2,-2}(ti)xy + \zeta_{2,-1}(ti)yz + \zeta_{2,0}(ti)(3z^2-1) + \zeta_{2,1}(ti)xz + \zeta_{2,2}(ti)(x^2-y^2) + \ldots$$

Here, $\zeta_{l,m}(ti)$ (l, m=0, ±1, ±2, . . . ) is a value of a coefficient at the time ti of each term. The reason of such decomposition is that a correction magnetic field generator and a gradient magnetic field coil (first-order term), which correct a vibrational error magnetic field, generate a magnetic field of a spatial change corresponding to the spherical harmonic term. Therefore, it is preferable to match the order of the spherical harmonic term to the specification of the correction magnetic field generator and the gradient magnetic field coil (first-order term) provided in the MRI apparatus to be corrected.

On the other hand, in the case of measuring a vibrational error magnetic field at the specific space coordinates as disclosed in PTL 3 or PTL 4, the vibrational error magnetic field is decomposed into terms that can be derived by each method.

As an effective and desirable example of decomposition, a vibrational error magnetic field is decomposed into a 0-th term and first-order terms so that the vibrational error magnetic field is corrected for each of their spherical harmonic terms. For example, when a test gradient magnetic field is applied to X, Y, and Z axes, the above is equivalent to calculating the spherical harmonic terms shown in the following table.

Most preferable analysis components

| Direction of test gradient magnetic field | Error magnetic field component to be calculated | Supplement |
| --- | --- | --- |
| X axis | 0-th order | Constant (B0) component |
|  | First order (X) | First-order variation component (X to X) parallel to test gradient magnetic field |
|  | First order (Y) | First-order variation component (X to Y) in Y-axis direction perpendicular to test gradient magnetic field |
|  | First order (Z) | First-order variation component (X to Z) in Z-axis direction perpendicular to test gradient magnetic field |
| Y axis | 0-th order | Constant (B0) component |
|  | First order (X) | First-order variation component (Y to X) in X-axis direction perpendicular to test gradient magnetic field |
|  | First order (Y) | First-order variation component (Y to Y) parallel to test gradient magnetic field |
|  | First order (Z) | First-order variation component (Y to Z) in Z-axis direction perpendicular to test gradient magnetic field |
| Z -axis | 0-th order | Constant (B0) component |
|  | First order (X) | First-order variation component (Z to X) in X-axis direction perpendicular to test gradient magnetic field |
|  | First order (Y) | First-order variation component (Z to Y) in Y-axis direction perpendicular to test gradient magnetic field |
|  | First order (Z) | First-order variation component (Z to Z) parallel to test gradient magnetic field |

In step 702, the error magnetic field calculation section 203 aligns the spherical harmonic term data of the vibrational error magnetic field, which has been calculated in step 701, in a time axis direction and performs multiplication using a window function w(k) in the time axis direction. That is, $\zeta_{l,m}(t_k) \leftarrow W(tk)\zeta_{l,m}(t_k)$.

The spherical harmonic term data obtained by the above multiplication of the window function is used for the subsequent analysis.

In the present embodiment, the definition expression of a desirable window function "Tukey Window" is shown below.

$$w(k) = \begin{cases} 1.0 & 0 \leq |k| \leq \alpha\frac{N}{2} \\ \frac{1}{2}\left[1 + \cos\left(\pi \cdot \frac{k - \alpha\frac{N}{2}}{2(1-\alpha)\frac{N}{2}}\right)\right] & \alpha\frac{N}{2} \leq |k| \leq N \end{cases}$$

K: integer

L = N + 1

Figure 8:
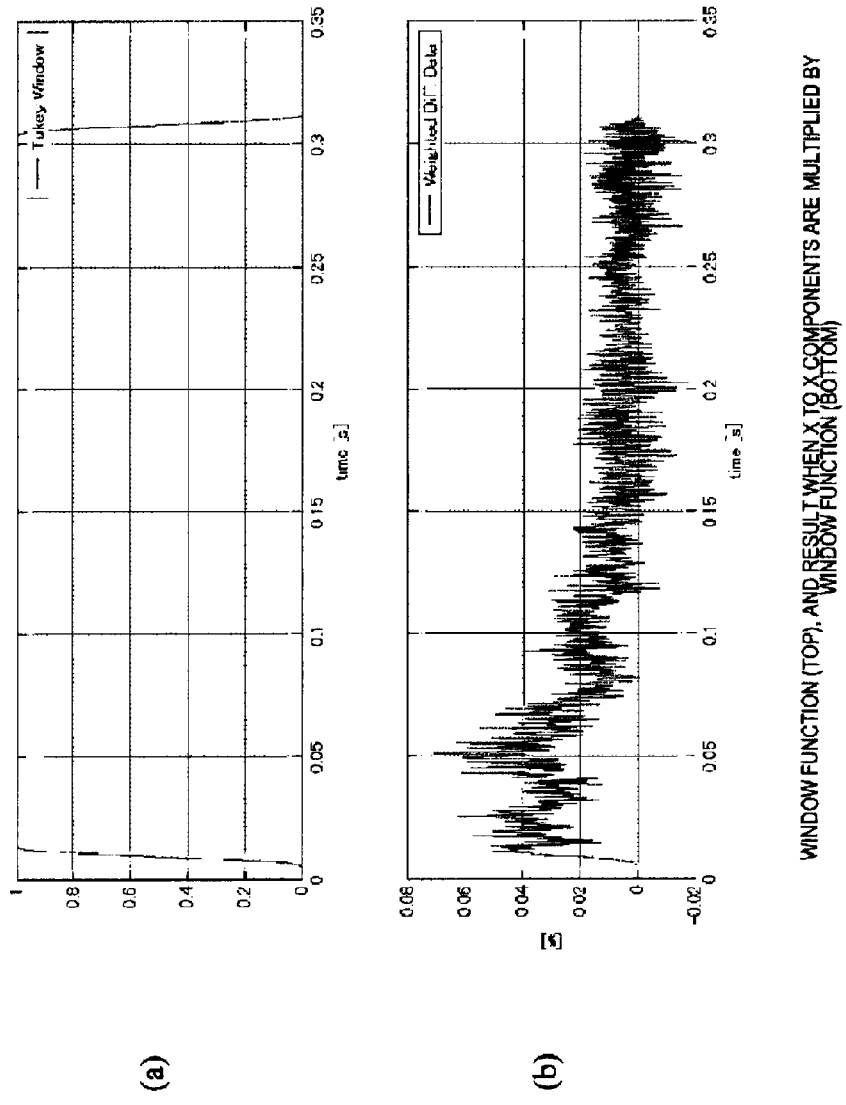
FIG. 8(a) is a view showing a Tukey Window.
FIG. 8(b) is a view showing an example where (X to X) terms of the vibrational error magnetic field are multiplied by a Tukey Window.

Here, L (Window Length) is the same size (length) as target analysis data, and α(0≤α≤1) is optimized by the target data. FIG. 8(a) shows Tukey Window, and FIG. 8(b) shows an example where (X to X) terms of the vibrational error magnetic field are multiplied by Tukey Window.

In addition, when a plurality of vibrational error magnetic field data items are present in a time direction due to shifting the signal acquisition start time or the like, portions overlapping each other along the time axis are assumed to be combined as one data item by averaging or the like.

Then, the error magnetic field calculation section 203 performs a frequency analysis in processing of following steps 703 to 705.

In step 703, the error magnetic field calculation section 203 performs a discrete Fourier transform using appropriate zero padding processing together for each item of the spherical harmonic term data of the vibrational error magnetic field multiplied by the window function in step 702.

Figure 9:
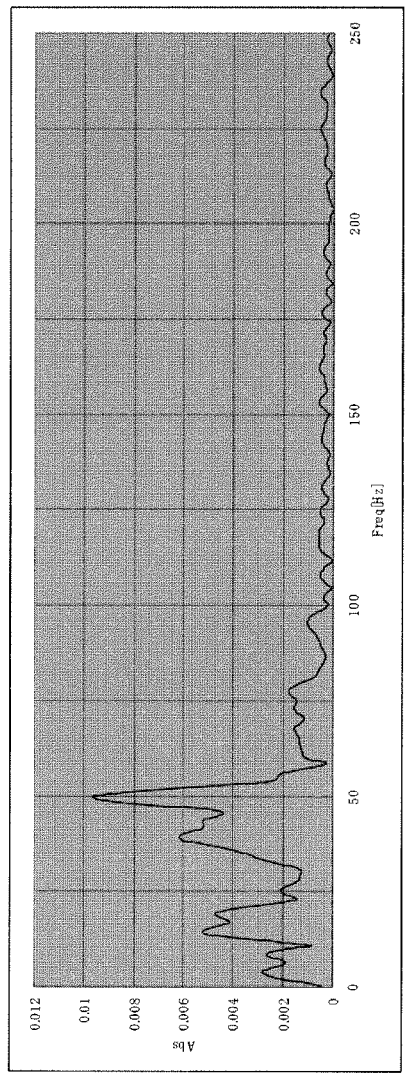
FIG. 9(a) is a view showing an example of the absolute value spectrum.
FIG. 9(b) is a view showing an example of the phase spectrum.
Figure 9:
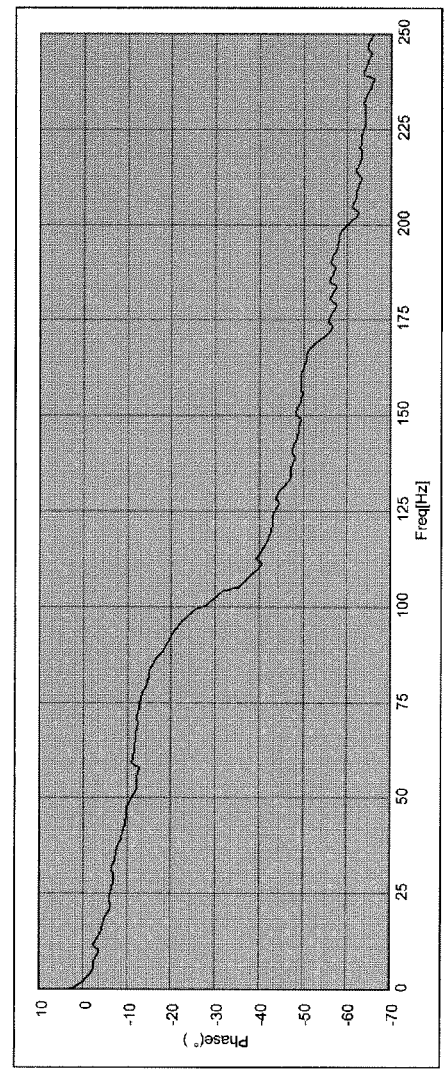

In step 704, the error magnetic field calculation section 203 creates an absolute value spectrum and a phase spectrum from the complex spectrum obtained by the discrete Fourier transform. In order to calculate a phase value from the complex data, it is preferable to use a known technique. For the phase spectrum, unwrapping processing may be performed. FIG. 9(a) shows an example of the absolute value spectrum regarding Y to X components, and FIG. 9(b) shows an example of the phase spectrum.

In step 705, the error magnetic field calculation section 203 performs frequency peak analysis for the frequency spectrum acquired in step 704. Then, matching the Lorentzian function of the frequency domain (Freq. Domain) and the damped vibration function of the time domain (Time Domain) mathematically through the Fourier transform is used. Then, the damped vibration function of the time domain corresponding to the parameter value of the Lorentzian function, which is obtained by approximating (that is, fitting) and expressing the spectrum shape near the frequency peak in the frequency domain with the Lorentzian function, is calculated.

The Lorentzian function having "frequency≤f" as a variable is defined by the following expression.
The Lorentzian Function $$F(f) = \frac{2\alpha}{4\pi^2(f-f_0)^2 + \alpha^2}$$

By using the Fourier transform, this function has the following correspondence relationship shown below with the time domain.

$$F(f) = \frac{2\alpha}{4\pi^2(f-f_0)^2 + \alpha^2} \Leftrightarrow f(t) = e^{-i(2\pi f_0 t)} \cdot e^{-\alpha \cdot t} = e^{-i(2\pi f_0 t)} \cdot e^{-t/\tau}$$
$$(t > 0)$$

Based on this relationship, the error magnetic field calculation section 203 performs a frequency peak analysis by applying (fitting) the Lorentzian function to the absolute value spectrum. When many significant frequency peaks are present, it is possible to perform nonlinear approximation using the Levenberg-Marquardt method or the Nelder-Mead method which is known mathematically.

In addition, in the frequency peak analysis, it is also possible to use a Gaussian function shown below instead of the Lorentzian function. It is preferable to use these functions appropriately according to the vibration characteristics.
The Gaussian Function $$F(f) = \sqrt{\frac{\pi}{a}} \cdot e^{-\frac{\pi^2 \cdot (f-f_0)^2}{a}}$$

$$F(f) = \sqrt{\frac{\pi}{a}} \cdot e^{-\frac{\pi^2 \cdot (f-f_0)^2}{a}} \Leftrightarrow f(t)e^{-i(2\pi f_0 t)} \cdot e^{-\alpha \cdot t^2} = e^{-i(2\pi f_0 t)} \cdot e^{-t^2/\tau}$$

If frequency peak identification is completed, the phase value at the peak frequency is read from the phase spectrum calculated in step 703-2. The accuracy of the phase spectrum may be improved by appropriately using complementary processing together according to the discrete value.

An attenuation constant $\tau$, a peak frequency $f_0$, a phase, and the like, which are parameter values obtained by the above frequency analysis, are stored in a storage unit, such as the magnetic disk 24, as characteristic values indicating the error magnetic field. These parameter values are read when calculating the output value of the correction magnetic field for correcting the vibrational error magnetic field in step 704, and are used for the calculation.

(Calculation of the Correction Magnetic Field)

Next, details of the correction magnetic field calculation for correcting the vibrational error magnetic field in step 304 will be described.

The error magnetic field correction section 204 calculates an output value of the correction magnetic field for correcting the vibrational error magnetic field according to the input gradient magnetic field waveform using each parameter value indicating the damped vibration function of the time domain calculated in step 705. Since a magnetic field component for correcting the vibrational error magnetic field is superimposed on the gradient magnetic field waveform, the error magnetic field correction section 204 may be additionally mounted in an eddy current correcting function (control board), which is already mounted in the measurement control unit 6 of the MRI apparatus, or the function may be newly added. From the perspective of the operating speed, calculation using hardware is desirable. However, if the processing speed is appropriate, the arithmetic processing unit 8 may perform an operation using software with the error magnetic field correction section 204 provided therein. Hereinafter, details of the correction magnetic field calculation will be described.

First, expression (formulation) of the output waveform of a correction magnetic field component will be described. Since the idea is the same for all correction components, a first-order gradient component of the vibrational error magnetic field will be representatively described.

An impulse response function $VGC^j(dl^j(s), t)$ with respect to the input gradient magnetic field waveform (differential value of the gradient magnetic field waveform at the j axis) $dl^j(S)$ is modeled as the following expression.

$$VGC^j(dl^j(s), t) = \sum_i dl^j(s) \cdot G_i^j \cdot \exp(i(2\pi f_i^j t + \phi_i^j)) \cdot \exp(-t/\tau_i^j) =$$
$$dl^j(s) \cdot \sum_i G_i^j \cdot \exp(i(2\pi f_i^j t + \phi_i^j)) \cdot \exp(-t/\tau_i^j)$$

When $t = 0$,
$$VGC^j(dl^j(s), t=0) = dl^j(s) \cdot \sum_i G_i^j \cdot \exp(i\phi_i^j)$$

Here, $VGC^j(dl^j(s), t)$ is a first-order vibration magnetic field in the j axis direction caused by $dl^j$, $G_i^j$ is vibration amplitude in the j axis direction determined by the ratio with respect to $dl^j$, $f_i^j$ is a vibration frequency, $\phi_i^j$ is an initial phase, $\tau_i^j$ is an attenuation time constant, t is time, i is a vibration component index, and j=(x y z).

In order to calculate the output of a correction component with respect to the input waveform of an arbitrary gradient magnetic field on the basis of this model, sequential response correction for the input waveform (differential value of the gradient magnetic field waveform) is considered as in the error magnetic field correction due to eddy current. The specific processing is shown in the following expression. When the input waveform $dI^j(t_k)$ is applied at the discontinuous time axis $t_k$ (k =0, 1, 2, ..., n), the vibrational error magnetic field at Time t is given by the following expression.

$$t = t_0$$
$$VGC^j(dI^j(t_0), t) = \sum_i dI^j(t_0) \cdot G_i^j \cdot \exp(i(2\pi f_i^j t + \phi_i^j)) \cdot \exp(-t/\tau_i^j)$$

$$t = t_1$$
$$VGC^j(dI^j(t_1), t) = VGC^j(dI^j(t_0), t = t_1 - t_0) + VGC^j(dI^j(t_1), t = 0)$$

$$t = t_2$$
$$VGC^j(dI^j(t_2), t) = VGC^j(dI^j(t_1), t = t_2 - t_1) + VGC^j(dI^j(t_2), t = 0)$$

$$\vdots$$

$$t = t_n$$
$$VGC^j(dI^j(t_n), t) = VGC^j(dI^j(t_{n-1}), t = t_n - t_{n-1}) + VGC^j(dI^j(t_n), t = 0)$$

(*) Note that this is a vector sum.

The vibrational error magnetic field is calculated when necessary as described above, and the real part is output as a correction value.

$$VGC_{out}^j(t) = Re[VGC^j(dI^j(t_n), t)]$$

Re [ . . . ]: real part

In addition, when the exponential function cannot be directly processed by the hardware, the following relational expression is used.

$$\exp(i\phi) = \cos(\phi) + i\sin(\phi)$$

(Calculation of the Correction Magnetic Field)

Next, details of the phase calibration of the correction magnetic field in step 305 will be described.

The phase calibration section 206 calculates the phase calibration value for performing the phase calibration of the output of the correction magnetic field calculated in step 704. When the phase calibration section 206 is mounted in the measurement control unit 6, the phase calibration of the correction magnetic field is performed using the phase calibration value calculated by the phase calibration section 206, and a correction magnetic field after the phase calibration is output to a correction magnetic field generator and a gradient magnetic field power source. When the phase calibration section 206 is mounted in the arithmetic processing unit 8, the calculated phase calibration value is notified to the measurement control unit 6. The measurement control unit 6 performs the phase calibration of the correction magnetic field calculated in step 704 using the phase calibration value, and outputs a correction magnetic field after the phase calibration to the correction magnetic field generator and the gradient magnetic field power source.

Figure 10:
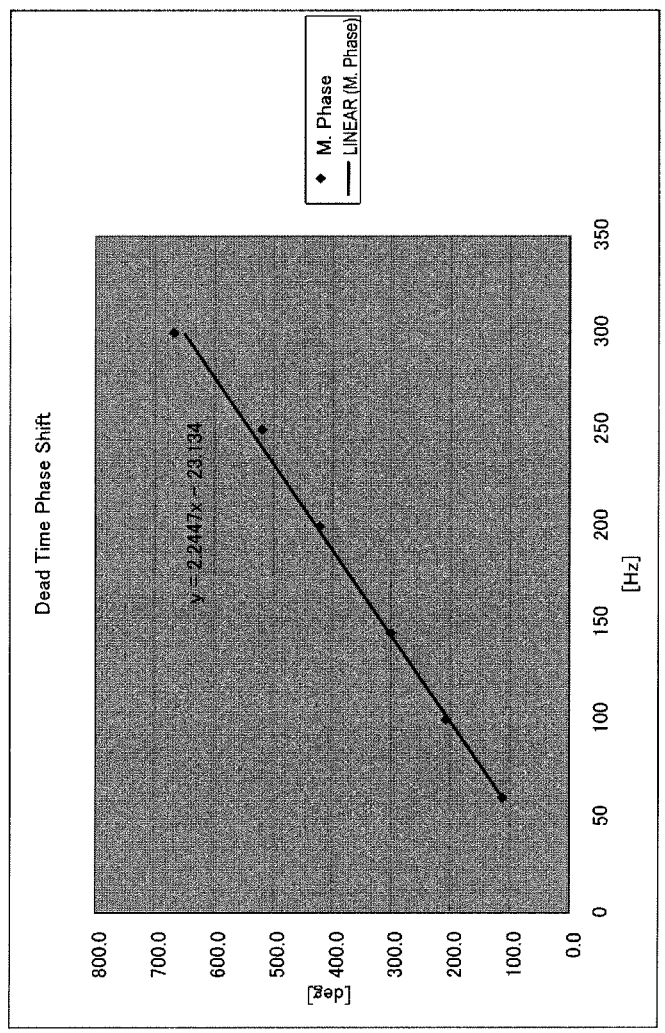
FIG. 10 is a graph showing an example of phase calibration data.

The purpose of the phase calibration is to cancel a phase error occurring between the output phase of the correction magnetic field calculated in step 704 and the phase at the frequency peak calculated in steps 703 to 705. For this reason, a phase value is measured for each frequency. The relationship between the frequency and the phase calibration value is stored in a magnetic disk or the like in advance, and the phase calibration section 206 performs the phase calibration of the correction magnetic field by reading the phase calibration value according to the frequency peak value calculated in step 703-3. FIG. 10 shows a graph of an example of phase calibration data. In this graph, the horizontal axis indicates a setting frequency, and the vertical axis indicates a measurement phase. The Y-intercept when the frequency is zero is equivalent to a phase error (offset).

As described above, the MRI apparatus and the vibrational error magnetic field reduction method of the present embodiment identify the frequency peak in the frequency spectrum of the vibrational error magnetic field and the waveform shape near the peak using a predetermined function, calculates correction magnetic field, which has an attenuation time constant corresponding to the parameter values obtained by the identification, according to the input gradient magnetic field waveform, and superimpose the calculated correction magnetic field on the gradient magnetic field and output the result. In this manner, it is possible to correct a vibrational error magnetic field due to the vibration of the mechanical structure of the MRI apparatus, which is caused not only by the application of eddy current magnetic field but also by the application of the gradient magnetic field. As a result, it is possible to improve the image quality.

Figure 11:
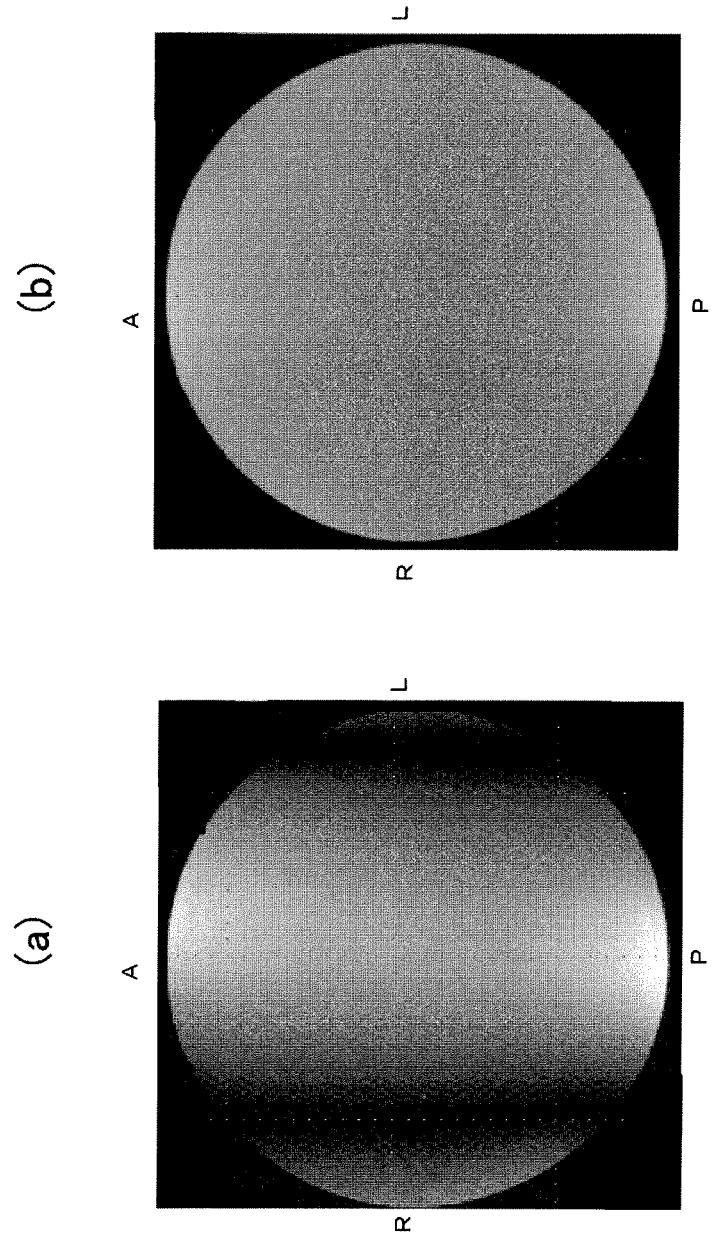
FIG. 11 is an image showing the effect of the present invention, where

Finally, FIG. 11 shows an example of the effect when the vibrational error magnetic field reduction of the present invention is actually applied. FIG. 11 shows images obtained by performing multi-slice imaging of the axial cross-section of a phantom using an FSE sequence (TR=733 msec, IET=8 msec, phase encoding direction=vertical direction). FIG. 11(*a*) is an image obtained without performing the vibrational error magnetic field reduction processing of the present invention, and FIG. 11(*b*) is an image obtained by performing the vibrational error magnetic field reduction processing of the present invention. By applying the vibrational error magnetic field reduction processing of the present embodiment, it is understood that image shading occurring at both ends in the horizontal direction is removed.

As can be understood by the above description of the embodiments of the present invention, the present invention has the following features. That is, an MRI apparatus of the present invention includes: a static magnetic field generation unit that generates a static magnetic field in imaging space; a gradient magnetic field generation unit that generates a gradient magnetic field so as to be superimposed on the static magnetic field; a correction magnetic field generation unit that generates a correction magnetic field for correcting an error magnetic field generated in the imaging space due to application of the gradient magnetic field; a structural unit that supports the static magnetic field generation unit, the gradient magnetic field generation unit, and the correction magnetic field generation unit mounted inside; a measurement control unit that measures an echo signal from an object disposed in the imaging space on the basis of a predetermined pulse sequence; and a correction magnetic field calculation unit that calculates a correction magnetic field for correcting an error magnetic field generated in the imaging space due to application of the gradient magnetic field. The correction magnetic field calculation unit calculates an error magnetic field including a vibrational error magnetic field based on vibration of the structural unit due to application of the gradient magnetic field, and calculates the correction magnetic field for correcting the calculated error magnetic field.

Preferably, a storage unit that stores characteristic values indicating the error magnetic field calculated by the correction magnetic field calculation unit is further provided, and the correction magnetic field calculation unit calculates the correction magnetic field on the basis of the stored characteristic values of the error magnetic field.

In addition, preferably, the correction magnetic field calculation unit includes: an error magnetic field measurement section that causes the measurement control unit to perform measurement of an echo signal using a pulse sequence having a test gradient magnetic field; an error magnetic field image acquisition section that acquires error magnetic field image data indicating an error magnetic field distribution at each sampling time using the echo signal; an error magnetic field calculation section that calculates a parameter value of a damped vibration function showing the error magnetic field using the error magnetic field image data; and a correction magnetic field calculation section that calculates the correction magnetic field on the basis of the calculated parameter value.

In addition, preferably, the error magnetic field measurement section acquires both information of the eddy current error magnetic field and information of the vibrational error magnetic field by making the measurement control unit measure an echo signal on which the information of the eddy current error magnetic field and the information of the vibrational error magnetic field are superimposed.

In addition, preferably, in the pulse sequence, an encoding gradient magnetic field pulse is applied in at least two axial directions, and the error magnetic field image acquisition section calculates error magnetic field image data at each sampling time using phase image data obtained by performing a Fourier transform of the echo signal in at least two axial directions every sampling time.

In addition, preferably, the error magnetic field measurement section causes the measurement control unit to perform measurement of the echo signal while changing the test gradient magnetic field, and the error magnetic field image acquisition section calculates error magnetic field image data at each sampling time using a difference between phase image data items, of which the test gradient magnetic fields are different, every sampling time.

In addition, preferably, the error magnetic field calculation section decomposes error magnetic field image data into a plurality of spherical harmonic terms and calculates a parameter value of a damped vibration function showing the error magnetic field for each spherical harmonic term, and the correction magnetic field calculation section calculates the correction magnetic field for each spherical harmonic term on the basis of the parameter value of the damped vibration function showing the error magnetic field for each spherical harmonic term.

In addition, preferably, the error magnetic field calculation section calculates the parameter value of the damped vibration function showing the error magnetic field by applying a Lorentzian function or a Gaussian function to a spectrum distribution, which is obtained by performing a Fourier transform of the error magnetic field image data in a time axis direction, for each spherical harmonic term.

In addition, preferably, the error magnetic field calculation section calculates a parameter value including an attenuation time constant of a damped vibration function of a time domain, which corresponds to a Fourier transform of the Lorentzian function or the Gaussian function, by applying the Lorentzian function or the Gaussian function to a waveform near a frequency peak in the spectrum distribution in a frequency domain.

In addition, preferably, the correction magnetic field calculation section creates a model of an impulse response function with respect to a gradient magnetic field waveform using the parameter value of the damped vibration function, and calculates the correction magnetic field as a sequential response of the model for an arbitrary input gradient magnetic field waveform.

In addition, preferably, a phase calibration section that calibrates a phase error between a phase of the correction magnetic field and a phase at the frequency peak of the spectrum distribution is further provided.

In addition, preferably, in the pulse sequence, the test gradient magnetic field is included before and after a re-convergence RF pulse, and the echo signal is measured after the test gradient magnetic field after the re-convergence RF pulse becomes zero.

A vibrational error magnetic field reduction method of the present invention is a vibrational error magnetic field reduction method of correcting a vibrational error magnetic field based on vibration of a structure of a magnetic resonance imaging apparatus, which is caused by application of a gradient magnetic field, using a correction magnetic field. The vibrational error magnetic field reduction method includes: a measurement step of measuring an echo signal using a pulse sequence having a test gradient magnetic field; an acquisition step of acquiring error magnetic field image data, which indicates an error magnetic field distribution at each sampling time, using the echo signal; a parameter value calculation step of calculating a parameter value of a damped vibration function showing the vibrational error magnetic field using error magnetic field image data at each sampling time; and a correction magnetic field calculation step of calculating the correction magnetic field on the basis of the calculated parameter value of the damped vibration function showing the vibrational error magnetic field.

In addition, preferably, in the parameter value calculation step, for a spectrum distribution obtained by performing a Fourier transform of the error magnetic field image data in a time axis direction at each sampling time, a parameter value of a damped vibration function showing the error magnetic field is calculated using a Lorentzian function or a Gaussian function.

In addition, preferably, in the parameter value calculation step, a damped vibration function of a time domain corresponding to a Lorentzian function or a Gaussian function applied to the spectrum distribution in a frequency domain is calculated, and a parameter value including an attenuation time constant of the damped vibration function is calculated.

In addition, preferably, in the correction magnetic field calculation step, a model of an impulse response function with respect to a gradient magnetic field waveform is created using the parameter value of the damped vibration function, and the correction magnetic field is calculated as a sequential response of the model for an arbitrary input gradient magnetic field waveform.

REFERENCE SIGNS LIST

1: gradient magnetic field generation system
2: static magnetic field generation system
3: signal transmission system
4: operating unit
5: signal receiving system
6: measurement control unit
7: signal processing system
8: arithmetic processing unit
9: object
10: gradient magnetic field coil
11: gradient magnetic field power source
12: high frequency oscillator
13: modulator 14: high frequency amplifier
15: RF transmission coil
16: RF receiving coil
17: signal amplifier
18: quadrature phase detector
19: A/D converter
20: ROM
21: RAM
22: magneto-optical disc
23: display
24: magnetic disk
25: track ball or mouse
26: keyboard

The invention claimed is:

1. A magnetic resonance imaging apparatus comprising:
a static magnetic field generation unit that generates a static magnetic field in imaging space;
a gradient magnetic field generation unit that generates a gradient magnetic field so as to be superimposed on the static magnetic field;
a correction magnetic field generation unit that generates a correction magnetic field or correcting an error magnetic field generated in the imaging space due to application of the gradient magnetic field;
a structural unit that supports the static magnetic field generation unit, the gradient magnetic field generation unit, and the correction magnetic field generation unit mounted inside;
a measurement control unit that measures an echo signal from an object disposed in the imaging space on the basis of a predetermined pulse sequence; and
a correction magnetic field calculation unit that calculates the correction magnetic field for correcting the error magnetic field generated in the imaging space due to application of the gradient magnetic field,
wherein calculations by the correction magnetic field calculation unit include calculating the error magnetic field including a vibrational error magnetic field based on vibration of the structural unit due to application of the gradient magnetic field, and calculating the correction magnetic field for correcting the calculated error magnetic field;
an error magnetic field measurement section that causes the measurement control unit to perform measurement of an echo signal using a pulse sequence having a test gradient magnetic field;
an error magnetic field image acquisition section that acquires error magnetic field image data indicating distribution of the error magnetic field at each sampling time using the echo signal;
an error magnetic field calculation section that calculates a parameter value of a damped vibration function showing the error magnetic field using the error magnetic field image data; and
a correction magnetic field calculation section that calculates the correction magnetic field on the basis of the calculated parameter value,
wherein the error magnetic field calculation section decomposes the error magnetic field image data into a plurality of spherical harmonic terms, calculates a parameter value including an attenuation time constant of the damped vibration function showing the error magnetic field by applying a Lorentzian function or a Gaussian function to a waveform near a frequency peak in a spectrum distribution in a frequency domain, which is obtained by performing a Fourier transform of the error magnetic field image data in a time axis direction, for each spherical harmonic term, and
the correction magnetic field calculation section calculates the correction magnetic field for each spherical harmonic term on the basis of the calculated parameter value of the damped vibration function showing the error magnetic field for each spherical harmonic term.

2. The magnetic resonance imaging apparatus according to claim 1, further comprising: a storage unit that stores characteristic values indicating the error magnetic field calculated by the correction magnetic field calculation unit, wherein the correction magnetic field calculation unit calculates the correction magnetic field on the basis of the stored characteristic values of the error magnetic field.

3. The magnetic resonance imaging apparatus according to claim 1,
wherein the error magnetic field measurement section acquires both information of eddy current error magnetic field and information of the vibrational error magnetic field by making the measurement control unit measure an echo signal on which the information of the eddy current error magnetic field and the information of the vibrational error magnetic field are superimposed.

4. The magnetic resonance imaging apparatus according to claim 1,
wherein, in the pulse sequence, an encoding gradient magnetic field pulse is applied in at least two axial directions, and the error magnetic field image acquisition section calculates error magnetic field image data at each sampling time using phase image data obtained by performing a Fourier transform of the echo signal in at least two axial directions every sampling time.

5. The magnetic resonance imaging apparatus according to claim 1,
wherein the error magnetic field measurement section causes the measurement control unit to perform measurement of the echo signal while changing the test gradient magnetic field, and the error magnetic field image acquisition section calculates error magnetic field image data at each sampling time using a difference between phase image data items, of which the test gradient magnetic fields are different, every sampling time.

6. The magnetic resonance imaging apparatus according to claim 1,
wherein the correction magnetic field calculation section creates a model of an impulse response function with respect to a gradient magnetic field waveform using the parameter value of the damped vibration function, and calculates the correction magnetic field as a sequential response of the model for an arbitrary input gradient magnetic field waveform.

7. The magnetic resonance imaging apparatus according to claim 1, further comprising:
a phase calibration section that calibrates a phase error between a phase of the correction magnetic field and a phase at the frequency peak of the spectrum distribution.

8. The magnetic resonance imaging apparatus according to claim 1,
wherein, in the pulse sequence, the test gradient magnetic field is included before and after a refocusing RF pulse, and the echo signal is measured after the test gradient magnetic field after the refocusing RF pulse becomes zero.

9. A vibrational error magnetic field reduction method of correcting a vibrational error magnetic field based on vibration of a structure of a magnetic resonance imaging apparatus, which is caused by application of a gradient magnetic field, using a correction magnetic field, the method comprising:

a measurement step of measuring an echo signal using a pulse sequence having a test gradient magnetic field;

an acquisition step of acquiring error magnetic field image data, which indicates an error magnetic field distribution at each sampling time, using the echo signal;

a parameter value calculation step of calculating a parameter value of a damped vibration function showing the vibrational error magnetic field using the error magnetic field image data at each sampling time; and a correction magnetic field calculation step of calculating the correction magnetic field on the basis of the calculated parameter value of the damped vibration function showing the vibrational error magnetic field, wherein, in the parameter value calculation step, the parameter value including an attenuation time constant of the damped vibration function showing the vibrational error magnetic field in a time domain and corresponding to a Lorentzian function or a Gaussian function applied to a spectrum distribution in a frequency domain obtained by performing a Fourier transform of the error magnetic field image data in a time axis direction at each sampling time is calculated.

10. The vibrational error magnetic field reduction method according to claim 9, wherein, the correction magnetic field calculation step, a model of an impulse response function with respect to a gradient magnetic field waveform is created using the parameter value of the damped vibration function, and the correction magnetic field is calculated as a sequential response of the model for an arbitrary input gradient magnetic field waveform.

11. A magnetic resonance imaging apparatus comprising:

a static magnetic field generation unit that generates a static magnetic field in imaging space;

a gradient magnetic field generation unit that generates a gradient magnetic field so as to be superimposed on the static magnetic field;

a correction magnetic field generation unit that generates a correction magnetic field for correcting an error magnetic field generated in the imaging space due to application of the gradient magnetic field;

a structural unit that supports the static magnetic field generation unit, the gradient magnetic field generation unit, and the correction magnetic field generation unit mounted inside;

a measurement control unit that measures an echo signal from an object disposed in the imaging space on the basis of a predetermined pulse sequence; and a correction magnetic field calculation unit that calculates the correction magnetic field for correcting the error magnetic field generated in the imaging space due to application of the gradient magnetic field, wherein the correction magnetic field calculation unit includes:

an error magnetic field measurement section that causes the measurement control unit to perform measurement of an echo signal using a pulse sequence having a test gradient magnetic field;

an error magnetic field image acquisition section that acquires error magnetic field image data indicating a distribution of the error magnetic field at each sampling time using the echo signal;

an error magnetic field calculation section that calculates a parameter value including an attenuation time constant of a damped vibration function showing the error magnetic field in a time domain and corresponding to a Lorentzian function or a Gaussian function applied to a spectrum distribution in a frequency domain, which is obtained by performing a Fourier transform of the error magnetic field image data in a time axis direction; and a correction magnetic field calculation section that calculates the correction magnetic field on the basis of the calculated parameter value of the damped vibration function showing the error magnetic field.

\* \* \* \* \*